US011089948B2

(12) United States Patent
Khettal et al.

(10) Patent No.: US 11,089,948 B2
(45) Date of Patent: Aug. 17, 2021

(54) OBJECTIVE LENS FOR AN ENDOSCOPE

(71) Applicant: avateramedical GmbH, Jena (DE)

(72) Inventors: Ali Khettal, Berlin (DE); Fabian Weise, Berlin (DE)

(73) Assignee: avateramedical GmbH

( * ) Notice: Subject to any disclaimer, the term of this patent is extended or adjusted under 35 U.S.C. 154(b) by 450 days.

(21) Appl. No.: 16/008,795

(22) Filed: Jun. 14, 2018

(65) Prior Publication Data

US 2018/0360298 A1  Dec. 20, 2018

(30) Foreign Application Priority Data

Jun. 16, 2017 (DE) .......................... 102017113273.2

(51) Int. Cl.
| | | |
|---|---|---|
| *A61B 1/00* | (2006.01) | |
| *G02B 23/24* | (2006.01) | |
| *A61B 1/002* | (2006.01) | |
| *G02B 1/10* | (2015.01) | |
| *G02B 5/04* | (2006.01) | |
| *G02B 13/00* | (2006.01) | |
| *G02B 1/11* | (2015.01) | |

(52) U.S. Cl.
CPC .......... *A61B 1/00179* (2013.01); *A61B 1/002* (2013.01); *A61B 1/00096* (2013.01); *A61B 1/00193* (2013.01); *G02B 1/10* (2013.01); *G02B 5/04* (2013.01); *G02B 23/243* (2013.01); *G02B 1/11* (2013.01); *G02B 13/0095* (2013.01)

(58) Field of Classification Search
USPC ................................................. 600/171, 166
See application file for complete search history.

(56) References Cited

U.S. PATENT DOCUMENTS

| | | | | |
|---|---|---|---|---|
| 4,178,075 A | * | 12/1979 | Rogers ............... | G02B 27/0025 359/648 |
| 4,621,910 A | | 11/1986 | Takahashi | |
| 4,838,247 A | * | 6/1989 | Forkner ............. | A61B 1/00181 600/171 |
| 4,850,342 A | * | 7/1989 | Hashiguchi ......... | A61B 1/0623 600/171 |
| 5,005,957 A | * | 4/1991 | Kanamori ............. | G02B 13/18 359/663 |
| 5,051,824 A | * | 9/1991 | Nishigaki .......... | A61B 1/00179 348/68 |

(Continued)

FOREIGN PATENT DOCUMENTS

| | | |
|---|---|---|
| CN | 105093515 | 11/2015 |
| JP | 05297272 A | 12/1993 |

*Primary Examiner* — Michael J Carey
*Assistant Examiner* — Shankar Raj Ghimire
(74) *Attorney, Agent, or Firm* — McGarry Bair PC

(57) ABSTRACT

An objective lens for an endoscope has an object-side lens element including a plane-convex rod lens and an image-side lens element including a biconvex lens arranged at the image-side end of the objective lens. The object-side lens element includes a plane-convex first lens and a biconcave second lens which form a front lens and are arranged in this order on the object side of the plane-convex rod lens forming a third lens. As viewed from the object side, the image-side lens element includes a biconvex fourth lens, a concave-plane fifth lens and a biconcave sixth lens which are arranged in this order on the object side of the biconvex lens that is arranged at the image-side end of the objective lens and forms a seventh lens.

15 Claims, 3 Drawing Sheets

(56) References Cited

U.S. PATENT DOCUMENTS

| | | | | |
|---|---|---|---|---|
| 5,377,669 A | | 1/1995 | Schulz | |
| 5,538,497 A | * | 7/1996 | Hori | A61B 1/00096 385/117 |
| 5,554,100 A | * | 9/1996 | Leiner | A61B 1/00179 385/117 |
| 5,599,278 A | * | 2/1997 | Hibbard | A61B 1/00142 600/133 |
| 5,689,365 A | * | 11/1997 | Takahashi | A61B 1/00179 359/362 |
| 5,825,534 A | * | 10/1998 | Strahle | A61B 1/00179 359/376 |
| 5,980,453 A | * | 11/1999 | Forkey | A61B 1/00193 600/162 |
| 6,139,490 A | * | 10/2000 | Breidenthal | A61B 1/00193 600/111 |
| 6,248,060 B1 | * | 6/2001 | Buess | A61B 1/00091 600/130 |
| 6,618,207 B2 | * | 9/2003 | Lei | G02B 23/243 359/656 |
| 7,160,247 B2 | * | 1/2007 | Deppmeier | A61B 1/00165 600/129 |
| 7,708,689 B2 | * | 5/2010 | Deppmeier | A61B 1/04 600/156 |
| 8,366,611 B2 | * | 2/2013 | Ivanovic | A61B 1/00179 600/176 |
| 10,054,772 B1 | * | 8/2018 | Zobel | G02B 13/0095 |
| 10,725,282 B2 | * | 7/2020 | Hegenbarth | G02B 23/243 |
| 2002/0091305 A1 | * | 7/2002 | Lederer | G02B 23/2423 600/171 |
| 2003/0083551 A1 | * | 5/2003 | Takahashi | A61B 1/00193 600/166 |
| 2009/0203963 A1 | | 8/2009 | Ito | |
| 2017/0119238 A1 | * | 5/2017 | Gao | G02B 9/06 |
| 2017/0235120 A1 | * | 8/2017 | Williamson | G02B 23/2415 348/45 |

\* cited by examiner

OBJECTIVE LENS FOR AN ENDOSCOPE

CROSS REFERENCE TO RELATED APPLICATION

This application claims the benefit of German Application DE 10 2017 113 273.2, filed on Jun. 16, 2017, which is incorporated herein in its entirety.

BACKGROUND

The invention relates to an objective lens for an endoscope having an object-side lens element including a plane-convex rod lens and an image-side lens element including a biconvex lens arranged at the image-side end of the objective lens. Further, the invention relates to a monocular endoscope or stereoscopic endoscope.

Endoscopes are in particular used in minimally invasive surgery to allow the operating surgeon insight into the body region in which the operating field is situated. At the distal end of an endoscope shaft, typically an objective lens is arranged, which collects the light originating from the object to be observed and generates a real intermediate image of the object. This intermediate image is transmitted by means of an optical relay system arranged downstream of the objective lens to the proximal end of the endoscope shaft. At the proximal end of the endoscope shaft, an eyepiece is arranged which images the real intermediate image either for the human eye or by means of a camera objective lens onto a sensor surface.

In particular in the case of rigid endoscopes, it is often difficult or even impossible to orient the endoscope such that the object to be observed lies on the axis of the rigid endoscope shaft. Typically, objective lenses are produced for this, which provide at least one beam deflection and thus allow an observation of objects that do not lie on the axis of the endoscope shaft.

Endoscopes in which the optical axis of object-side lens elements is angled with respect to the axis of the endoscope shaft are referred to in the following as angled-view endoscopes. In contrast thereto, endoscopes that only allow an observation of objects that substantially lie on the axis of the endoscope shaft are referred to as straight-view endoscopes.

From document CN 105093515 A, an objective lens for a straight-view endoscope is known, which comprises two lens elements, of which the lens element arranged at the object side includes a glass rod as well as a plane-convex rod lens and the lens element arranged at the image side includes a biconvex lens. Document CN 105093515 A further discloses an objective lens for an angled-view endoscope. The beam deflection required for this is implemented with the aid of a prism.

In document U.S. Pat. No. 5,051,824 A, likewise an objective lens for an angled-view endoscope is disclosed.

SUMMARY OF THE INVENTION

Starting from the known prior art, it is the object of the invention to specify an objective lens for an endoscope that has a simple and compact structure with a high optical quality.

This object is solved by an objective lens having the features of claim 1 and a monocular endoscope or stereoscopic endoscope having the features of claim 15. Advantageous developments are specified in the dependent claims.

The inventive objective lens for an endoscope comprises an object-side lens element including a plane-convex rod lens and an image-side lens element including a biconvex lens arranged at the image-side end of the objective lens. The object-side lens element includes a plane-convex first lens and a biconcave second lens which form a front lens and are arranged in this order on the object side of the plane-convex rod lens forming a third lens. As viewed from the object side, the image-side lens element includes a biconvex fourth lens, a concave-plane fifth lens and a biconcave sixth lens which are arranged in this order on the object side of the biconvex lens that is arranged at the image-side end of the objective lens and forms a seventh lens.

The optical elements of the inventive objective lens advantageously interact to generate an intermediate image of high optical quality. In particular, the specific design of the image-side lens element generates an intermediate image with a defined negative image field curvature. This image field curvature can be corrected by further optical elements, in particular an optical relay system and an eyepiece, such that an image without significant image field curvature (or with a small distortion and/or free from astigmatism) is obtained. The objective lens according to the invention further comprises only a few components or optical component parts and thus has a simple and compact structure. As a result, a simple and compact structure with high optical quality is achieved. In particular, the objective lens according to the invention has a comparably small diameter, for example with a field of view (FOV) of greater than 70°.

In an advantageous embodiment, the biconvex fourth lens, the concave-plane fifth lens, the biconcave sixth lens and/or the biconvex seventh lens of the image-side lens element are cemented to each other. By using cemented lenses, in the following also referred to as cemented elements, the production and assembly cost can be considerably reduced. In particular, the entire image-side lens element can be formed as one single component.

In a further advantageous embodiment, the plane-convex first lens and the biconcave second lens of the object-side lens element are cemented to each other. These two lenses together are also referred to as front lens in the following. The front lens can in particular be formed as an achromatic lens. Further, the biconcave second lens can be cemented to the plane-convex third lens. As a result, the object-side lens element can be formed as one single component.

It is advantageous when the optical axis of the front lens is angled with respect to a longitudinal axis of an endoscope shaft of the endoscope when between the biconcave second lens and the plane-convex third lens a prism is arranged such that it causes a beam deflection from the optical axis of the front lens to the longitudinal axis of the endoscope shaft of the endoscope, and when the prism is cemented to the plane-convex third lens. Embodiments with a prism for beam deflection are also referred to in the following as angled-view objective lenses to distinguish them from straight-view objective lenses without a prism.

In an advantageous development of the angled-view objective lens, a plane-parallel glass plate which is cemented to the biconcave second lens and the prism is arranged between the biconcave second lens and the prism. The plane-parallel glass plate can in particular be formed such that the length of the path in glass of the angled-view objective lens is extended to the length of the path in glass of the straight-view objective lens. When the length of the path in glass of the object-side lens element in the straight-view objective lens is equal to the length of the path in glass in the angled-view objective lens, then the image-side lens element can be identically formed in both embodiments.

In an advantageous development of the straight-view objective lens, a glass rod, in particular with two plane-parallel surfaces, is arranged between the front lens and the plane-convex third lens. The glass rod can be cemented to the plane-convex third lens and the biconcave second lens. By the arrangement of the glass rod it is achieved that the plane-convex third lens has the same length both in embodiments for a straight view and in embodiments for an angled view, without the length of the objective lens having to be adapted as a whole.

Preferably, the plane-convex first lens, the biconcave second lens, the glass rod and/or the plane-convex third lens of the object-side lens element and/or the prism and/or the plane-parallel glass plate and/or the biconvex fourth lens, the concave-plane fifth lens, the biconcave sixth lens and/or the biconvex seventh lens of the image-side lens element are made of flint glass.

The plane-convex first lens, the glass rod, the plane-convex third lens, the plane-parallel glass plate, the biconvex fourth lens, the concave-plane fifth lens, the biconcave sixth lens and/or the biconvex seventh lens for example have an antireflection coating. The antireflection coating serves to reduce scattered light and an associated deterioration of the optical quality of the objective lens. Further, the antireflection coating also increases the optical transmission.

The prism in particular has a high-reflection coating on those surfaces on which light is reflected for beam deflection. Such a coating reduces light loss by means of transmission upon reflection.

In an advantageous development, the plane-convex first lens, the biconcave second lens, the prism and/or the plane-parallel glass plate are surrounded by a material such that the respective diameter of the element is matched to the diameter of the plane-convex third lens and/or the glass rod. Thus, it can be achieved that the optical component parts of the objective lens have a common diameter, which facilitates the assembly and increases the optical and mechanical stability.

Further, it is advantageous when on the object side of the front lens a plane-parallel disk is arranged, which is, for example, made of sapphire. The use of sapphire is advantageous owing to its optical properties, in particular the high transmission level in the relevant wavelengths, its chemical properties (in particular sapphire is chemically inert) and its mechanical properties, in particular its scratch and wear resistance.

In a further advantageous development, the objective lens has a mechanical separation point between the object-side lens element and the image-side lens element.

The mechanical separation point makes it possible to replace the object-side lens element in a particularly easy manner by an otherwise formed object-side lens element. By the provision of different, mechanically mounted object-side lens elements in designs for a straight view and an angled view, endoscopes with different views can be implemented particularly easily.

The invention further relates to a stereoscopic objective lens for use in a stereoscopic endoscope. The stereoscopic objective lens comprises two objective lenses of the above-described type.

A further aspect of the invention relates to a monocular endoscope or stereoscopic endoscope. The monocular endoscope comprises an objective lens as previously described. The stereoscopic endoscope comprises the just mentioned stereoscopic objective lens.

Further features and advantages of the invention result from the following description which explains the invention in more detail on the basis of embodiments in connection with the enclosed Figures.

DRAWINGS

Figure 1:
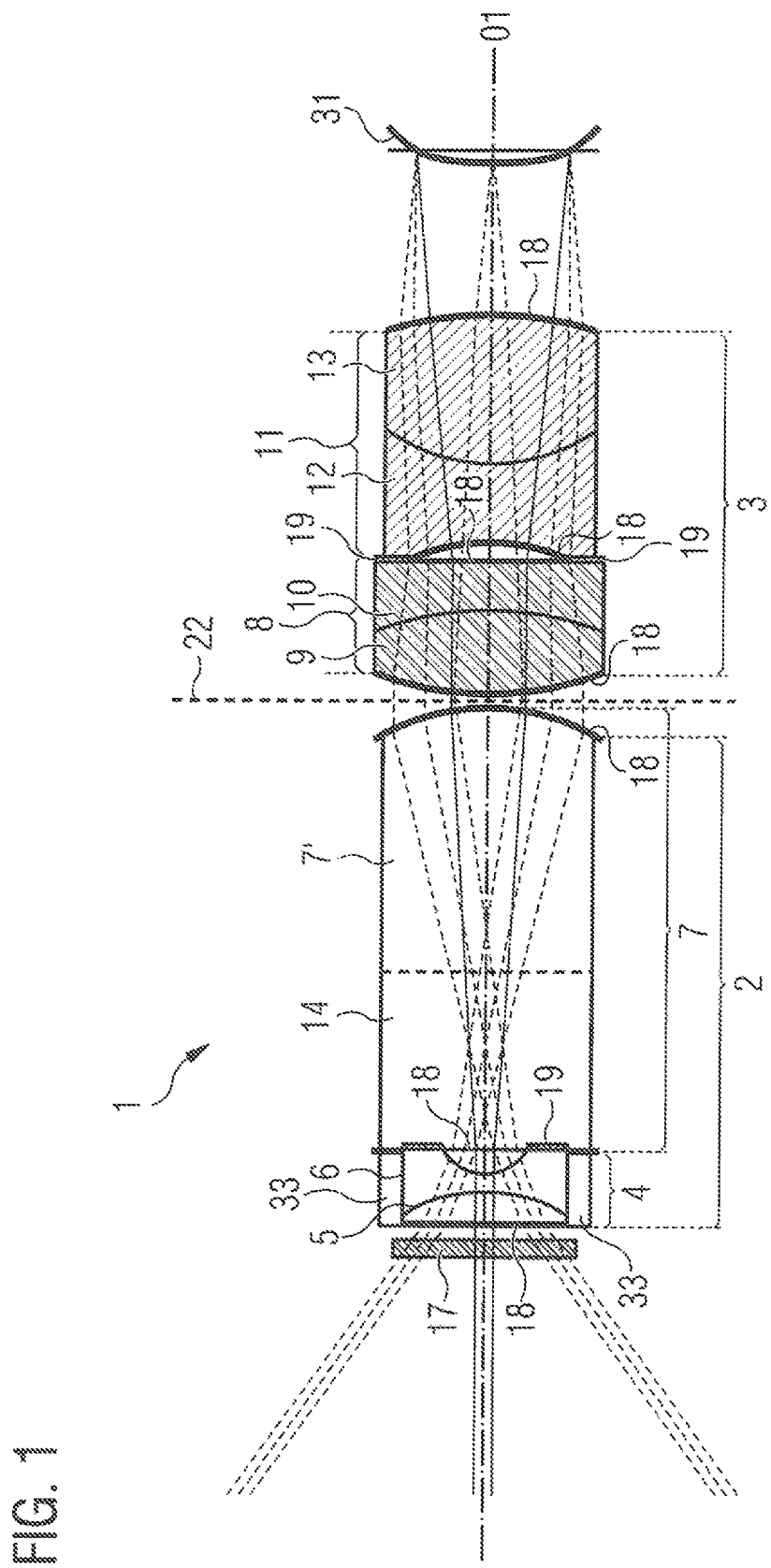
FIG. 1 shows an embodiment of an objective lens for an endoscope.

FIG. 1 shows an embodiment of an objective lens 1 for an endoscope 24, 25 in a schematic illustration. In the shown embodiment, the objective lens 1 is a straight-view objective lens, i.e. the shown embodiment is suited for observing objects which substantially lie on an axis O1 of an endoscope shaft not shown in FIG. 1.

DESCRIPTION

The objective lens 1 includes a lens element 2 arranged on the object side and a lens element 3 arranged on the image side. The object-side lens element 2 is separated from the image-side lens element by a mechanical separation point 22.

As viewed from the object side, the object-side lens element 2 comprises a front lens 4, a glass rod 14 with two plane-parallel surfaces and a plane-convex third lens 7 formed as a rod lens. The front lens 4 is formed by a plane-convex first lens 5 and a biconcave second lens 6. The two lenses 5, 6 of the front lens 4 are cemented to each other. The front lens 4 is cemented to the glass rod 14. Further, the glass rod 14 is cemented to the plane-convex third lens 7 so that the object-side lens element 2 forms one single component part. A sapphire glass window 17 is arranged on the object side of the front lens 4.

As viewed from the object side, the image-side lens element 3 comprises a first lens group 8 and a second lens group 11. As viewed from the object side, the first lens group 8 comprises a biconvex fourth lens 9 and a concave-plane fifth lens 10 which are cemented to each other. As viewed from the object side, the second lens group 11 comprises a biconcave sixth lens 12 and a biconvex seventh lens 13 which are likewise cemented to each other. For example, the two lens groups 8, 11 of the image-side lens element 3 are connected to each other by cementing the concave-plane fifth lens 10 and the biconcave sixth lens 12 so that the image-side lens element 3 forms one single component part. However, in the embodiment according to FIG. 1, the two lens groups 8, 11 of the image-side lens element 3 are not cemented.

The front lens 4, the plane-convex third lens 7, the biconvex fourth lens 9 of the first lens group 8, the concave-plane fifth lens 10 of the first lens group 8 and the biconvex seventh lens 13 of the second lens group 11 have an antireflection coating 18 on the non-cemented surfaces. Further, the objective lens 1 has blackened surfaces 19 on the biconcave second lens 6 and the concave-plane fifth lens 10. The plane-convex first lens 5 and the biconcave second lens 6 are surrounded by a material 33 such that the respective diameter of the element is matched to the diameter of the plane-convex third lens 7 and/or the glass rod 14.

The first lens group 8 and the second lens group 11 of the image-side lens element 3 form, if taken alone, one achromatic field lens each. The image-side lens element 3 generates a chromatically corrected intermediate image 31 with a defined, negative image field curvature. The mechanical separation point 22 allows the easy exchange of the object-side lens element 2. The blackened surfaces 19 have the effect of stops in the objective lens 1 (in particular each time as a stop for scattered light minimization and not as a field stop or aperture).

Table 1 shows the lens data of the objective lens 1 according to FIG. 1. The optically effective surfaces are numbered in Table 1 with 1 to 10 from the object side. All length information is expressed in the unit [mm]. The names of the glasses are in accordance with the nomenclature of Schott.

In Table 2, the paraxial optical data of the objective lens 1 according to FIG. 1 are shown.

TABLE 1

| Surface | Radius | Thickness | Glass | Diameter |
|---|---|---|---|---|
| Object | Indefinite | 50 | | 74.43 |
| 1 | Indefinite | 0.5 | N-LASF46A | 2.8 |
| 2 | −2.84 | 0.3 | N-BAF4 | 2.8 |
| 3 | 8.85 | 0.368 | | 1.4 |
| 4 | Indefinite | 7.3 | N-LASF44 | 3.6 |
| 5 | −3.15 | 0.306 | | 3.6 |
| 6 | 5.4 | 1.4 | N-LAF21 | 3.6 |
| 7 | −3.7 | 0.7 | N-SF6 | 3.6 |
| 8 | Indefinite | 0.447 | | 3.6 |
| 9 | −2.92 | 1.1 | N-SF1 | 3.6 |
| 10 | 2.92 | 2.5 | N-LASF31 | 3.6 |

TABLE 2

| | |
|---|---|
| Focal length | 1.91 mm |
| NA | 0.086 |
| Field angle | 72 |
| ø Image (diagonal) | 2.50 mm |
| Radius of the image field curvature | −2.65 mm |
| ø Optical system | 3.60 mm |

Figure 2:
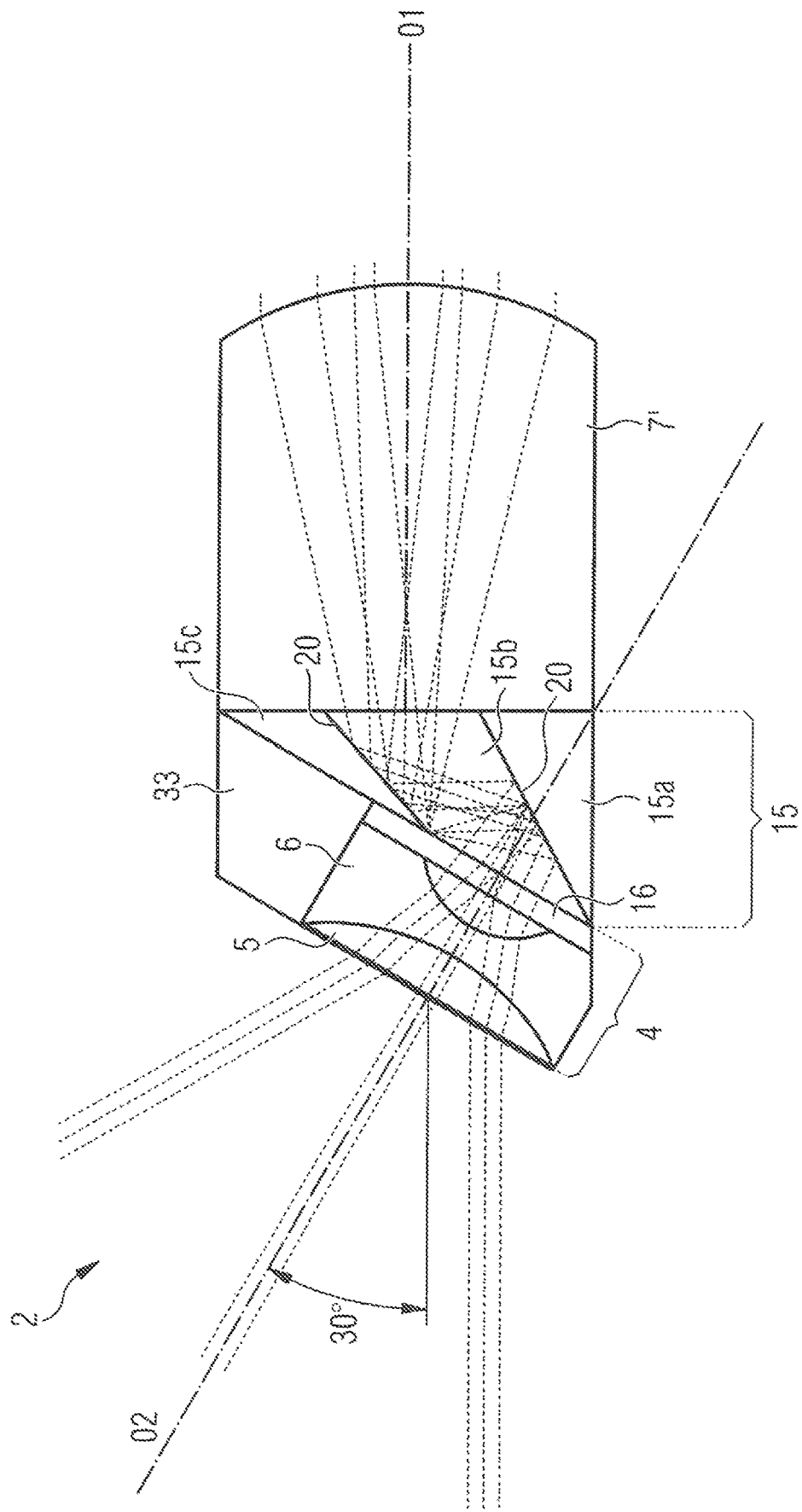
FIG. 2 shows an embodiment of an image-side lens element for the objective lens according to FIG. 1.

FIG. 2 shows an embodiment of the object-side lens element 2 for the objective lens 1 according to FIG. 1. The object-side lens element 2 shown in FIG. 2 is suitable for use in an angled-view objective lens. The objective-side lens element 2 according to FIG. 2 differs from the object-side lens element 2 according to FIG. 1 substantially by a prism 15 arranged between the front lens 4 and the plane-convex third lens 7. Further, here the object-side lens element 2 comprises a plane-parallel glass plate 16 which is arranged between the front lens 4 and the prism 15. The prism 15 is formed by three elements 15*a*, 15*b*, 15*c*, only one (15*b*) of which being optically effective. The surfaces of the prism 15 that reflect light entering into the objective lens 1, for example have a high-reflection coating 20. In the embodiment shown, the two outer elements 15*a*, 15*c*, on the contrary, have a lower fraction index than the inner element 15*b*, as a result whereof a total reflection at the boundary interfaces can be realized. A high-reflection coating is thus not absolutely necessary in the embodiment according to claim 1. The plane-convex first lens 5, the biconcave second lens 6, the prism 15 and the plane-parallel glass plate 16 are surrounded by the material 33 such that the respective diameter of the element is matched to the diameter of the plane-convex third lens 7.

The prism 15 implements a beam deflection from the optical axis O2 of the front lens 4 to the axis O1 of the endoscope shaft not shown in FIG. 2. The tilt enables an observation of objects that do not lie on the axis O1 of the endoscope shaft. A tilt of the axes by 30° is exemplarily shown, but also other tilt angles are conceivable, for example 15°, 45° or 90°. The plane-parallel glass plate 16 provides that the length of the path in glass of the object-side lens element 2 according to FIG. 2 corresponds to the length of the path in glass of the object-side lens element 2 according to FIG. 1. Here, the path in glass in particular corresponds to the path that is covered by the light within the optical element. As a result, in both embodiments the image-side lens element 3 shown in FIG. 1 can be used together with the respective object-side lens element 2. The mechanical separation point 22 of the objective lens 1 according to FIG. 1 allows the exchange of the object-side lens element 2 of the objective lens 1, for example by the object-side lens element 2 according to FIG. 2, to implement an endoscope 24 with angled view. The endoscope 24 can thus easily be adapted to different needs.

Figure 3:
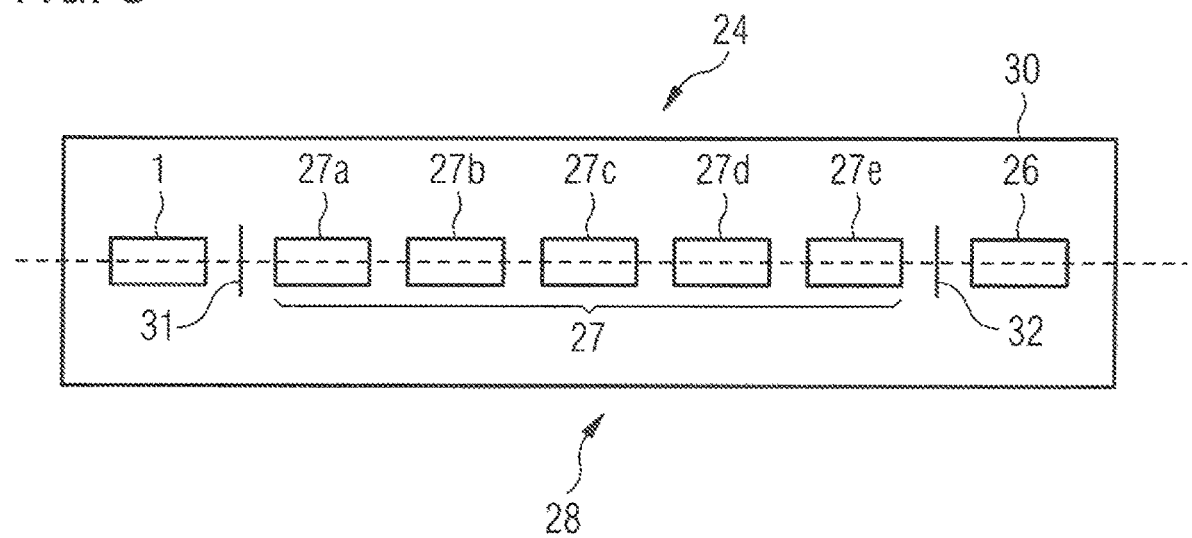
FIG. 3 shows an embodiment of a monocular endoscope including an objective lens according to FIG. 1.

In FIG. 3, an embodiment of a monocular endoscope 24 is shown, which includes the objective lens 1 according to FIG. 1. As viewed from the object side, the monocular endoscope 24 comprises an objective lens 1, an optical relay system 28 with a relay module 27 with several relay module components 27*a* to 27*e* and an eyepiece 26. Further, the endoscope 24 has a shaft 30, in which the afore-mentioned elements are arranged.

The objective lens 1 arranged at the distal end of the endoscope 24 generates a first intermediate image 31 of the object to be observed. The relay system 27 images the distal first intermediate image 31 onto a proximal second intermediate image 32. Thus, the relay system 27 transfers the first intermediate image 31 so to speak from the distal to the proximal end of the endoscope 24. The eyepiece 26 arranged at the proximal end of the endoscope 24 finally images the second intermediate image 32 onto a camera sensor not shown in FIG. 3.

The distal intermediate image 31 generated by the objective lens 1 has a negative image field curvature. The optical relay system 28 is designed to correct the negative image field curvature of the objective lens 1. The image of the endoscope 24 thus has no or only a negligible image field curvature with a compact structure of all optical component parts.

Figure 4:
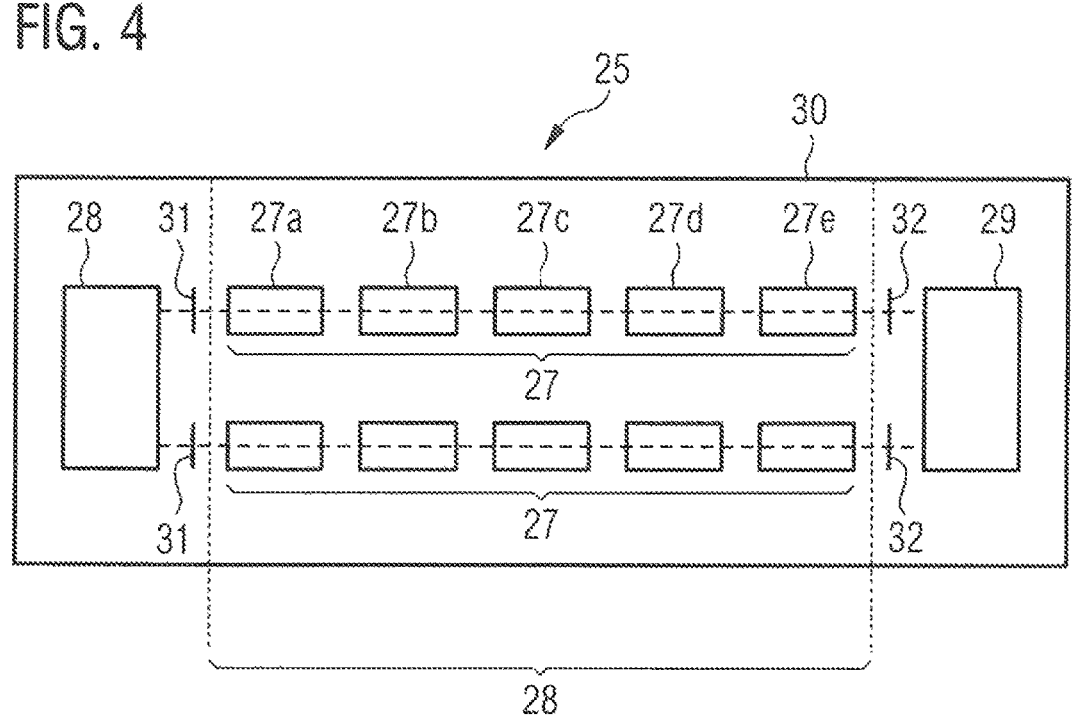
FIG. 4 shows an embodiment of a stereoscopic endoscope including two objective lenses according to FIG. 1.

An embodiment of a stereoscopic endoscope 25 is schematically illustrated in FIG. 4. In contrast to the monocular endoscope 24 illustrated in FIG. 3, the stereoscopic endoscope 25 has two optical channels. The stereoscopic endoscope 25 has a shaft 30 in which, as viewed from the distal end, an objective lens 23, an optical relay system 28 with two relay modules 27 for each of the two optical channels (stereoscopic relay system) and a proximally arranged eyepiece 29 are arranged.

The objective lens 23 is formed by two objective lenses 1 according to FIG. 1. One of the two objective lenses 1 each is assigned to one of the optical channels. Each of the two objective lenses 1 generates a first intermediate image 31 from the object to be observed. The stereoscopic relay system 28 according to FIG. 2 images one of the two distal intermediate images 31 each on one of the two proximal intermediate images 32 each. The proximal intermediate images 32 generated in this way are then imaged onto a camera sensor not shown in FIG. 4 by the eyepiece 29.

The invention claimed is:

1. An objective lens for an endoscope comprises an object-side lens element including a plane-convex rod lens and an image-side lens element including a single biconvex lens arranged at an image-side end of the objective lens, wherein, as viewed from an object side of the objective lens,
the object-side lens element further includes a single plane-convex first lens and a single biconcave second lens which form a front lens arranged in this order on an object side of the plane-convex rod lens which forms a third lens, and
the image-side lens element further includes a single biconvex fourth lens, a single concave-plane fifth lens and a single biconcave sixth lens arranged in this order on an object side of the single biconvex lens that is arranged at the image-side end of the objective lens and which forms a seventh lens.

2. The objective lens according to claim 1, characterized in that the single plane-convex first lens and the single biconcave second lens and the single plane-convex third lens of the object-side lens element are cemented to each other.

3. The objective lens according to claim 1, characterized in that the single biconvex fourth lens, the single concave-plane fifth lens, the single biconcave sixth lens and/or the single biconvex seventh lens of the image-side lens element are cemented to each other.

4. The objective lens according to one of the claim 1, characterized in that the plane-convex third lens is formed by a single plane-convex rod lens and a single glass rod which are cemented to each other.

5. The objective lens according to claim 4, characterized in that the single glass rod is made of flint glass and/or has an antireflection coating.

6. The objective lens according claim 1, characterized in that the optical axis of the front lens is angled with respect to a longitudinal axis of an endoscope shaft of the endoscope, that between the single biconcave second lens and the single plane-convex third lens a prism is arranged such that it causes a beam deflection from the optical axis of the front lens to the longitudinal axis of the endoscope shaft of the endoscope, and that the prism is cemented to the plane-convex third lens.

7. The objective lens according to claim 6, characterized in that between the single biconcave second lens and the prism a plane-parallel glass plate is arranged and cemented thereto.

8. The objective lens according to claim 6, characterized in that the prism has a high-reflection coating.

9. The objective lens according to claim 1, characterized in that the single plane-convex first lens, the single biconcave second lens, the plane-convex third lens, the single biconvex fourth lens, the single concave-plane fifth lens, at least one of the single biconcave sixth lens or the single biconvex seventh lens is made of flint glass.

10. The objective lens according to claim 1, characterized in that at least one of the single plane-convex first lens, the single biconcave second lens, the plane-convex third lens, the single biconvex fourth lens, the single concave-plane fifth lens, the single biconcave sixth lens or the single biconvex seventh lens has an antireflection coating.

11. The objective lens according to claim 1, characterized in that the single plane-convex first lens and the single biconcave second lens are radially surrounded by a material such that the diameter of the front lens and the diameter of the plane-convex third lens are matched.

12. The objective lens according to claim 1, characterized in that a sapphire glass window is arranged on the object side of the single plane-convex first lens.

13. The objective lens according to claim 1, wherein between the object-side lens element and the image-side lens element a mechanical separation point for exchanging the object-side lens element is arranged.

14. A stereoscopic objective lens comprising two objective lenses, each objective lens having an object-side lens element including a plane-convex rod lens and an image-side lens element including a single biconvex lens arranged at an image-side end of the objective lens,
wherein, as viewed from the object side of the objective lens,
each object-side lens element includes a single plane-convex first lens and a single biconcave second lens which form a front lens arranged in this order on an object side of the plane-convex rod lens which forms a third lens, and
the image-side lens element includes a single biconvex fourth lens, a single concave-plane fifth lens and a single biconcave sixth lens arranged in this order on an object side of the biconvex lens that is arranged at the image-side end of the objective lens and which forms a seventh lens.

15. An endoscope comprising at least one objective lens having an object-side lens element including a plane-convex rod lens and an image-side lens element including a single biconvex lens arranged at an image-side end of the objective lens,
wherein, as viewed from the object side of the objective lens,
the object-side lens element includes a single plane-convex first lens and a single biconcave second lens which form a front lens arranged in this order on an object side of the plane-convex rod lens which forms a third lens, and
the image-side lens element includes a single biconvex fourth lens, a single concave-plane fifth lens, and a single biconcave sixth lens arranged in this order on an object side of the biconvex lens that is arranged at the image-side end of the objective lens and which forms a seventh lens.

* * * * *